(12) United States Patent
Ubelacker et al.

(10) Patent No.: US 10,703,223 B2
(45) Date of Patent: Jul. 7, 2020

(54) SEAT OCCUPANCY RECOGNITION

(71) Applicant: GRAMMER AG, Amberg (DE)

(72) Inventors: Roland Ubelacker, Pfreimd (DE); Jens Kolb, Konigstein (DE); Achim Kullmann, Amberg (DE)

(73) Assignee: GRAMMER AG, Amberg (DE)

(*) Notice: Subject to any disclaimer, the term of this patent is extended or adjusted under 35 U.S.C. 154(b) by 0 days.

(21) Appl. No.: 16/302,171

(22) PCT Filed: May 3, 2017

(86) PCT No.: PCT/EP2017/060463
§ 371 (c)(1),
(2) Date: Nov. 16, 2018

(87) PCT Pub. No.: WO2017/198459
PCT Pub. Date: Nov. 23, 2017

(65) Prior Publication Data
US 2019/0143844 A1   May 16, 2019

(30) Foreign Application Priority Data

May 17, 2016  (DE) .................. 10 2016 109 008
May 17, 2016  (DE) .................. 10 2016 109 013
Mar. 31, 2017  (DE) .................. 10 2017 106 949

(51) Int. Cl.
*B60N 2/00*   (2006.01)
*B60N 2/75*   (2018.01)
*A61B 5/024*  (2006.01)
*G01G 19/00*  (2006.01)
*G06K 9/00*   (2006.01)
(Continued)

(52) U.S. Cl.
CPC .............. *B60N 2/002* (2013.01); *A61B 5/024* (2013.01); *A61B 5/0205* (2013.01); *B60N 2/75* (2018.02); *B60N 2/79* (2018.02); *G01G 19/00* (2013.01); *G01V 11/002* (2013.01);
(Continued)

(58) Field of Classification Search
CPC ......... A61B 5/0205; A61B 5/024; A61B 5/08; A61B 5/1123; B60N 2/002; B60N 2/75; B60N 2/79; G01G 19/00; G01V 11/002; G06K 9/00342; G06K 9/00838
See application file for complete search history.

(56) References Cited

U.S. PATENT DOCUMENTS

2007/0120347 A1* 5/2007 Breed .................... B60N 2/002
                                              280/735
2007/0135982 A1  6/2007 Breed et al.
(Continued)

OTHER PUBLICATIONS

International Search Report prepared by the European Patent Office dated Jul. 13, 2017, for International Application No. PCT/EP2017/060463.

*Primary Examiner* — Omer S Khan
(74) *Attorney, Agent, or Firm* — Sheridan Ross PC

(57) ABSTRACT

The invention relates to a seat occupancy recognition device for recognising the occupancy of a seat, characterised by at least one volume detection device with at least one first sensor which is provided and designed to detect a volume on the vehicle seat, and at least one body function detection device with at least one second sensor, which is provided and designed to detect body functions, and at least one body function recognition device for recognising the detected body functions.

14 Claims, 9 Drawing Sheets

Figure 1A:
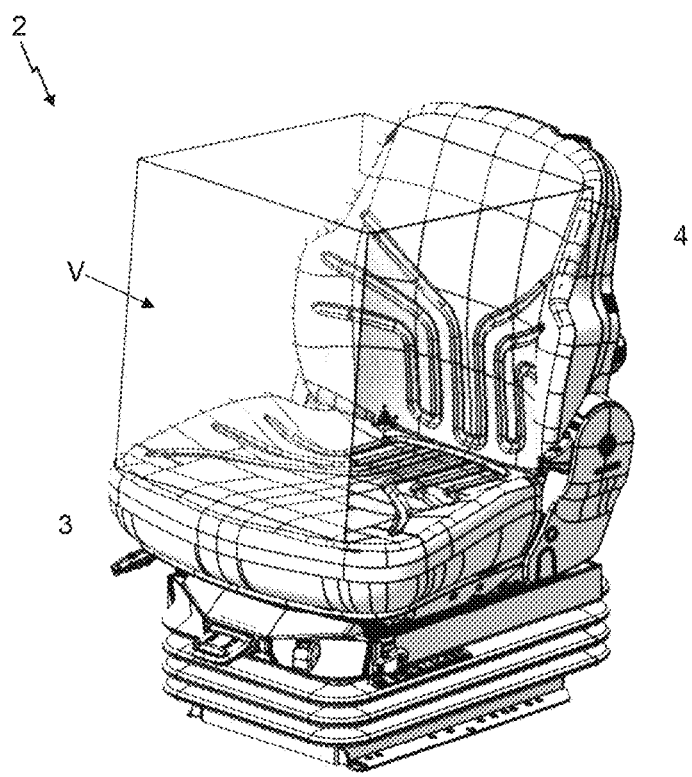

(51) Int. Cl.
*A61B 5/0205* (2006.01)
*G01V 11/00* (2006.01)
*A61B 5/08* (2006.01)
*A61B 5/11* (2006.01)

(52) U.S. Cl.
CPC ..... *G06K 9/00342* (2013.01); *G06K 9/00838* (2013.01); *A61B 5/08* (2013.01); *A61B 5/1123* (2013.01)

(56) References Cited

U.S. PATENT DOCUMENTS

| | | | |
|---|---|---|---|
| 2014/0211985 A1* | 7/2014 | Polese | G06K 9/00362 |
| | | | 382/103 |
| 2015/0202991 A1* | 7/2015 | Sugiyama | B60N 2/90 |
| | | | 340/575 |
| 2017/0055884 A1* | 3/2017 | Takeuchi | A61B 5/1124 |
| 2017/0262675 A1* | 9/2017 | Suman | G06K 7/10732 |

* cited by examiner

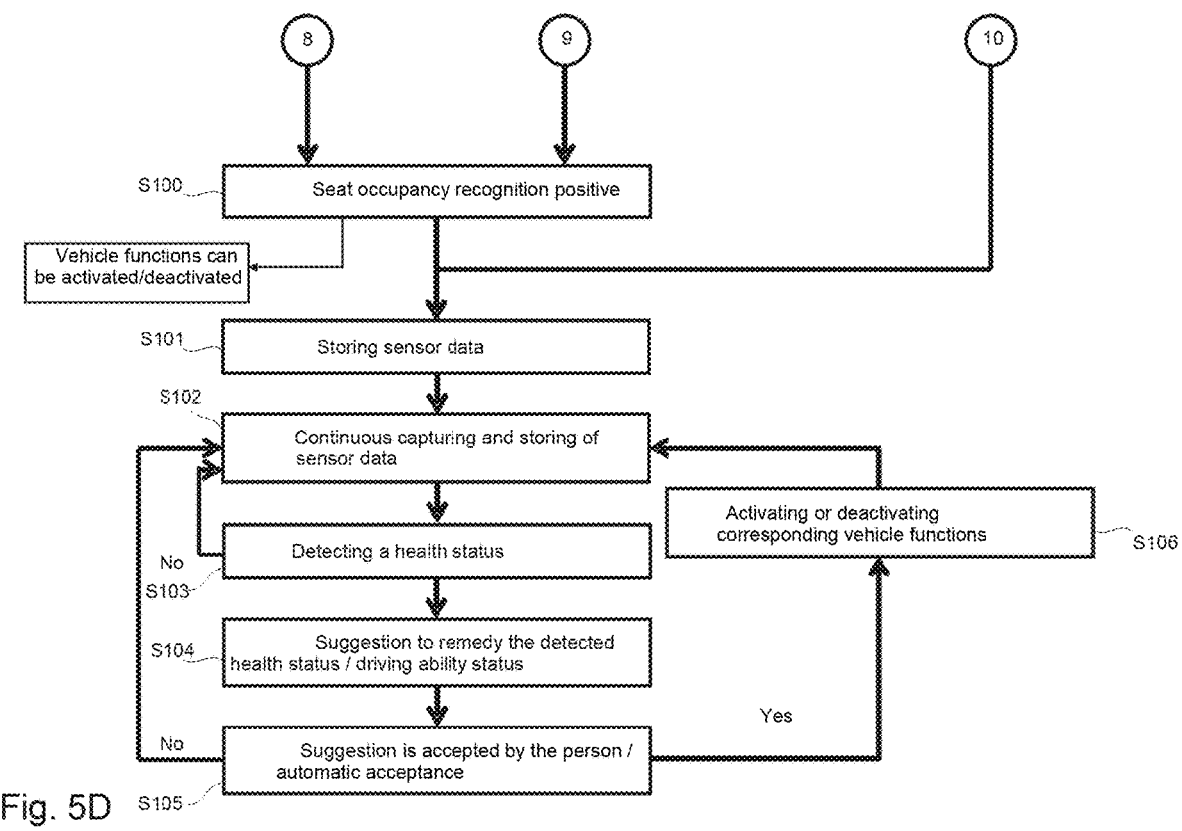

us 10,703,223 B2

SEAT OCCUPANCY RECOGNITION

CROSS REFERENCE TO RELATED APPLICATIONS

This application is a national stage application under 35 U.S.C. 371 and claims the benefit of PCT Application No. PCT/EP2017/060463 having an international filing date of 3 May 2017, which designated the United States, which PCT application claimed the benefit of German Patent Application No. 10 2016 109 008.5 filed 17 May 2016, German Patent Application No. 10 2016 109 013.1 filed 17 May 2016, and German Patent Application No. 10 2017 106 949.6 filed 31 Mar. 2017, the entire disclosures of each of which are incorporated herein by reference.

DESCRIPTION

The invention relates to seat occupancy recognition for a vehicle seat, particularly commercial vehicle seats, and a method for recognizing seat occupancy.

Vehicle seats are known from prior art, by means of which one can detect whether a vehicle seat is occupied or not. Simple seats with seat occupancy recognition use sensor data from a sensor, by means of which a weight on the vehicle seat can be detected, and then simply conclude from this that the seat is occupied by a person.

However, this method and the vehicle seat respectively according to prior art are unable to detect precisely whether a person, an animal or some other object, such as a case of beer, is positioned on the commercial vehicle seat.

Therefore, the object of the present invention is to provide seat occupancy recognition as well as a vehicle seat, particularly a commercial vehicle seat, having seat occupancy recognition, and a method by means one can detect whether a person is sitting on a vehicle seat and occupying it.

The core idea of this invention is to provide a method for recognizing seat occupancy of a seat, wherein the method comprises the method steps:
a. Performing volume detection for detecting a volume on the vehicle seat by means of a volume detection device,
b. Performing body function detection by means of a body function detection device after positively detecting a volume.

According to the invention, the method for recognizing seat occupancy of a seat, particularly a commercial vehicle seat, thereby comprises a first method step of volume detection by means of a volume detection device.

A volume refers to at least a partial volume of a human body. By means of a volume detection device, one can therefore detect that at least a partial volume of the human body is located on the vehicle seat. A volume can hereby also be detected by mass detection and/or contour detection, since a volume can also be inferred by such detection methods.

Advantageously, the volume detection device comprises at least one sensor, which is provided and designed to detect a volume, so that a volume can be detected, for example also by contours or mass. Such a sensor may be designed as a capacitive sensor, an inductive sensor, a light barrier, an electromagnetic sensor or an ultrasound sensor or a combination thereof. Preferably, a capacitive sensor is hereby involved, by means of which an electric field can be generated. If a volume is thereby placed in the sensor range of the sensor or if a volume is located there, the value of the electric flux density belonging to the electric field changes due to the change of the dielectric conductivity through the volume.

However, when using volume detection by means of a volume detection device, one can still not differentiate whether a person or an object is on the vehicle seat. Therefore, it is necessary that the method comprises additional method steps by means of which one can decide whether a person or an inanimate object is on the vehicle seat.

According to the invention, the method therefore also advantageously comprises a second method step for detecting body functions by means of a body function detection device.

Body functions hereby refer in a particularly advantageous manner to a cardiac function and/or pulmonary function. By means of the body function detection device, one can hereby detect a heartbeat using a heart rate and/or a pulse, or a respiratory rate. Also, a movement, for example of body parts, of the volume can be detected for this purpose.

In addition, one can also detect other body functions for example, such as the temperature of the vehicle driver, the weight of the vehicle driver, the oxygen content of the blood of the vehicle driver, perspiration of the vehicle driver, a body contour, body movement, gastric acoustics, brainwaves, muscle signals, skin resistance, body odor and the like.

Depending on the body functions to be detected, the body function detection device thereby comprises corresponding sensors, which can record in an optical, electrical, magnetic, electromagnetic, thermal, and mechanical manner, as well as other sensor data.

According to a particularly preferred embodiment, the method comprises a third method step of performing body function recognition by means of a body function recognition device after positive body function detection. This method step verifies whether the sensor data recorded by the body function detection device can be attributed to a human body. One can hereby exclude that an animal is on the vehicle seat and that it is in fact a human being. Thus, positive body function detection hereby refers to the fact that body functions were detected. Preferably, these are biosignals and/or body movements, and preferably these body functions therefore involve a cardiac and/or pulmonary function as examples of biosignals, since these are particularly characteristic for the animate beings identified. By means of body function detection, one can detect whether an animate being is on the vehicle seat, and, in particular, one can detect whether a person is on the vehicle seat. Biosignals and/or body movements are utilized for differentiation purposes If seat occupancy recognition is positive, in other words if it was detected that a person is on the vehicle seat, the sensor data recorded by the body function detection device can be used for additional functions that extend beyond seat occupancy recognition.

According to another preferred embodiment, after body function recognition is negative, either the body function detection is repeated, or method step a. is continued, or additional body functions are detected by the body function detection device. In other words, this means that either method step b. is performed again, or method steps a. and b., or additional body functions are detected, which can be used to make a decision as to whether the detected volume on the vehicle seat is a person or not.

According to another embodiment, the additional body function is at least one selected from a temperature, perspiration, gastric acoustics, body odor, brainwaves and/or a combination thereof.

In this way, it is conceivable for example that at least a portion of the recorded sensor data of the seat occupancy recognition process, particularly the body function detection device, is shown to the vehicle driver by means of a display or the like. In this way, vehicle drivers can check their current heart rate or pulse, their current respiration rate or the like, and if applicable, based on the current data shown, they can check or monitor their current physical condition.

Furthermore, it is also conceivable that by means of the body function recognition device, particularly after positive body function detection, one can also detect what the current health status of the vehicle driver is. By means of deviations of the current heart or respiration rate compared to previously recorded values or sensor data, one can determine for example, depending on the deviation, that the driver is tired or becoming tired, or that the driver is stressed. Furthermore, it is also conceivable that one can detect that a driver is perspiring or that the driver is too hot. Naturally, other options are also conceivable.

Advantageously, the detected deviation can also be shown to the driver and corresponding to his current health status, a remedy can be displayed to the driver. For example, if the vehicle drivers are too hot so that they are perspiring increasingly, this is then detected, and the drivers are notified accordingly with the suggestion that the air-conditioning system should be activated to counteract the increased perspiration. On the other hand, if the drivers are stressed, their pulse, or heart rate, will go up as well as the breathing rate. If a stressful situation is detected, the driver can be notified for example to turn off the vehicle. Furthermore, a driver's life-threatening health condition, such as cardiac arrest or the like, can be detected. If such a health condition were identified, the vehicle as well as the vehicle seat with all available functions is preferably deactivated so that no other individuals are injured or objects are damaged.

All in all, vehicle functions and/or vehicle seat functions can be controlled as a function of the sensor data captured. Advantageously, the functions are not automatically activated or deactivated, however; instead, the driver is initially notified, for example by a depiction on a display or the like, and the functions are activated or deactivated only after confirmation by the driver. In particular for positive seat occupancy recognition, the vehicle functions are released for the vehicle driver, i.e., the vehicle functions can be activated or deactivated by means of actuation.

Preferably, the method step of measuring body functions is carried out only after the method step of detecting the volume, and in a particularly preferred manner the method step of measuring the body functions is carried out only after the method step of detecting the volume is positive. This means that a volume must first be detected before a decision is made whether an object or an animate being, preferably a human, is involved.

The object of the present invention is also achieved by a seat occupancy recognition device, comprising at least one volume detection device having a first sensor, which is provided and designed for detecting a volume on the vehicle seat, and at least one body function detection device having a second sensor, which is provided and designed for measuring body functions, particularly after detecting a volume. According to the invention, the volume detection device and the body function detection device each comprise at least one sensor, by means of which a volume or body functions can be detected. In a further preferred manner, the seat occupancy recognition device has at least one body function detection device for recognizing the detected body functions.

By means of the volume detection device, one can detect a mass in an alternative or cumulative manner, so that seat occupancy recognition is detected if a mass is located on the vehicle seat. In a further alternative or cumulative manner, one can also recognize contours in order to detect seat occupancy.

Furthermore, sensors or sensor devices are also conceivable, which can detect or register seat occupancy and a body function simultaneously, wherein naturally the recorded signals must be correctly read and processed by such sensors or sensor devices.

According to a preferred embodiment, by means of the first sensor of the volume detection device, at least one of the processes of contour detection and mass detection can also be carried out.

According to another preferred embodiment, by means of the second sensor of the body function detection device, at least one of the functions of cardiac function and pulmonary function can be detected, particularly one of the functions of the heart rate, pulse and breathing rate.

In a further advantageous manner, the seat occupancy recognition device comprises a storage device by means of which the sensor data recorded by the volume detection device and the body function detection device can be stored.

According to the invention, the seat occupancy recognition device comprises a body function detection device for detecting body functions. In this way, the recorded body functions can be advantageously attributed to a person and one can thereby exclude that the seat is occupied by an animal.

According to another preferred embodiment, the second sensor is designed and provided to record sensor data and transmit these to the body function detection device, wherein the body function detection device can execute a comparison of the sensor data against previously recorded sensor data to determine a health status.

By comparing sensor data against previously recorded sensor data, one can possibly observe a deviation from a target value or a trend in the values, and one can draw a conclusion from the corresponding observation. For example, one can conclude from a continuous increase of the body temperature that the driver is too hot, for example.

Also advantageously, the seat occupancy recognition device comprises a control device, which is preferably connected to the volume detection device and the body function detection device at least in a signal-related manner. By means of the control device, volume detection can first be initiated by means of the volume detection device, followed by a body function detection after volume detection has been performed. In particular, the output of the volume detection can be further utilized by the control device. If the volume detection is negative, no body function detection is possible, for example, since the basic prerequisite for seat occupancy does not exist.

However, if volume detection is positive, then body function detection is initiated by the control device.

In a particularly advantageous manner, seat occupancy recognition is active as long as the vehicle, particularly the vehicle functions, are active or activatable.

For example, a vehicle can be considered active even if no engine has been started yet, but the ignition has already been activated, since activating the ignition already makes many vehicle functions available.

It is conceivable that seat occupancy recognition is performed continuously as long as the vehicle is active. Alternatively, it is also conceivable that seat occupancy recognition is performed based on regular or irregular time periods. Of course, the time periods can hereby be selected and adjusted correspondingly. An excessively long time span could result in bypassing seat occupancy recognition, which is naturally not desired because of safety-related issues.

It is also conceivable that seat occupancy recognition is performed when a certain event occurs; seat occupancy recognition is event-triggered, such as by activating vehicle functions.

In a particularly preferred manner, the volume detection device and the body function detection device are designed in such a manner that contact-free detection or sensing of the corresponding volume and the corresponding body functions are possible. Naturally, contact-free detection or sensing is also conceivable; however, it is more convenient for a vehicle driver when contact-free detection or measurement is possible.

In a particularly preferred manner, the first and second sensor are each selected from optical, electrical, magnetic, electromagnetic, thermal, capacitive, acoustic or mechanical sensors.

Furthermore, a body function detection device can be provided, by means of which one can detect whether the recorded sensor data can be attributed to a person or not. In this way, one can exclude that an animal is on the seat for example and seat occupancy recognition is thereby bypassed.

Furthermore, the seat occupancy recognition device can comprise storage or a storage device, by means of which the recorded sensor data can be stored. These stored values can then be retrieved for an additional use, for example to depict the trend of a heart rate or breathing rate, or to detect certain health conditions by a comparison against previously recorded sensor data.

In a further preferred manner, the sensors used involve either passive or active sensors, wherein passive sensors are preferred, since seat occupancy recognition is to be designed as simply as possible and should not unnecessarily complicate the circuit or the structure of the vehicle seat, if possible.

Additional advantageous embodiments emerge from the dependent claims.

Figure 1B:
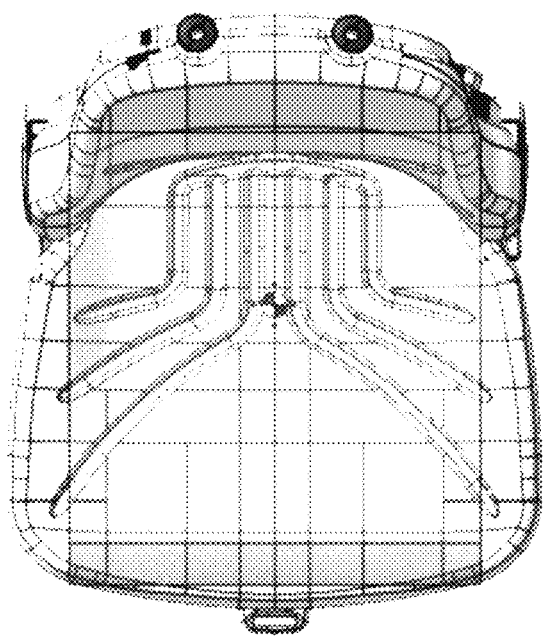
Figure 1C:
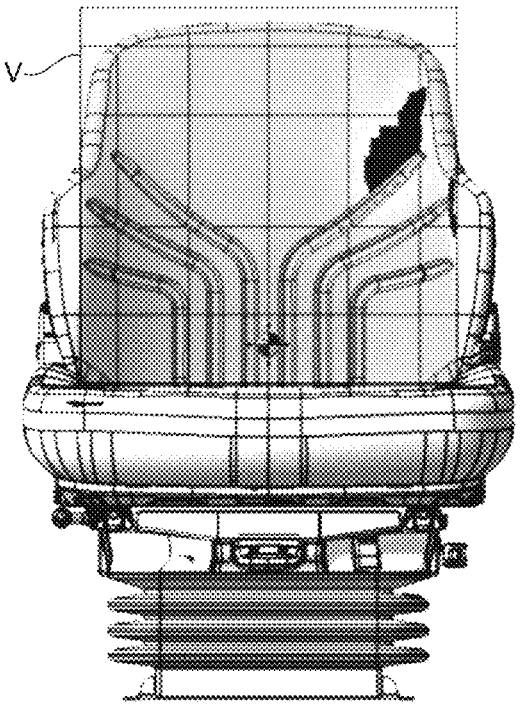
Figure 1D:
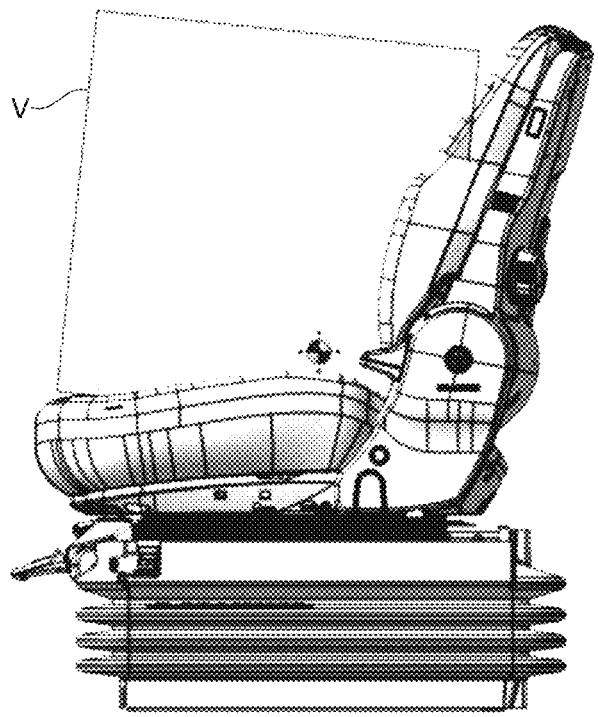
Figure 2:
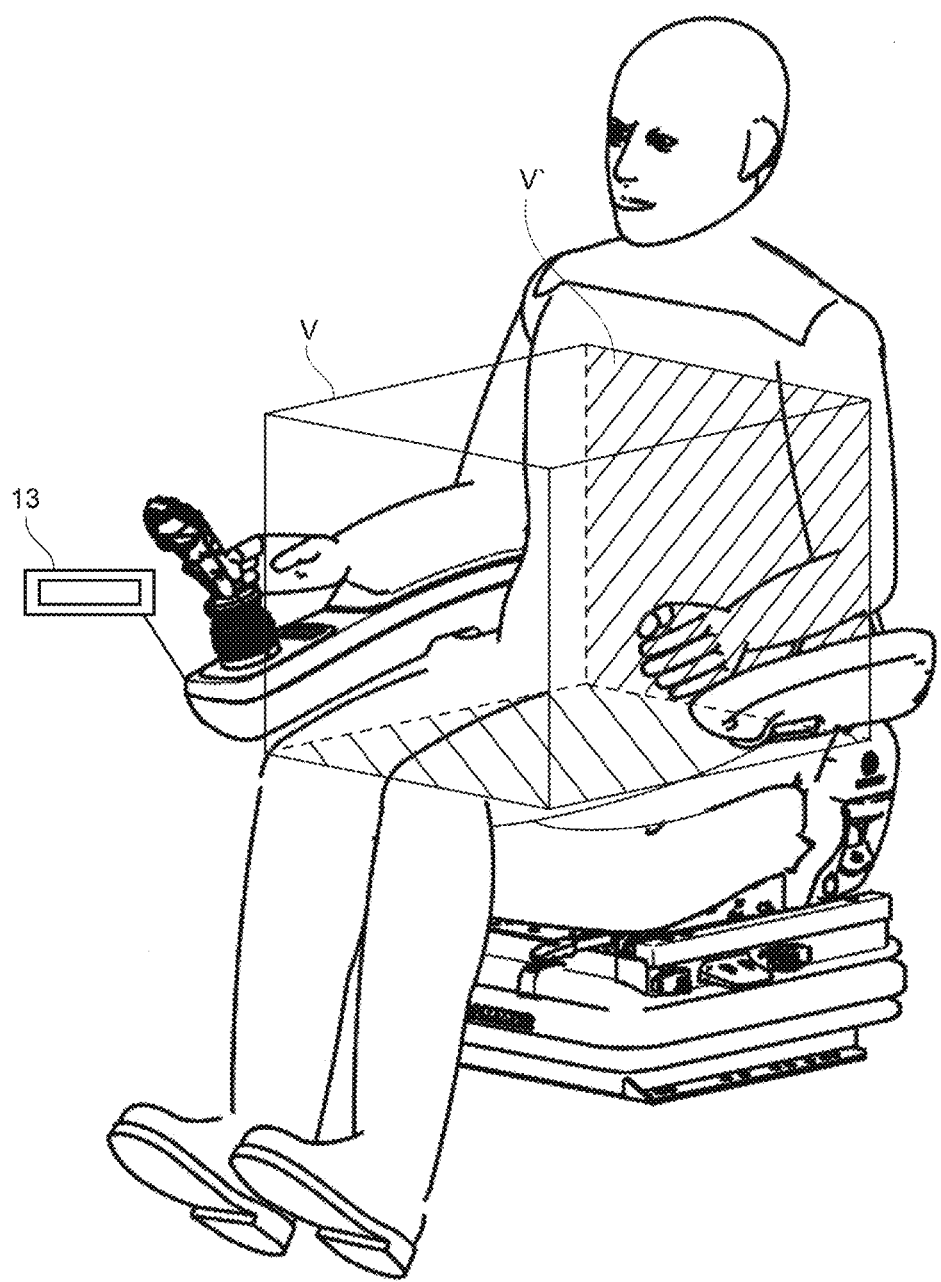
Figure 3:
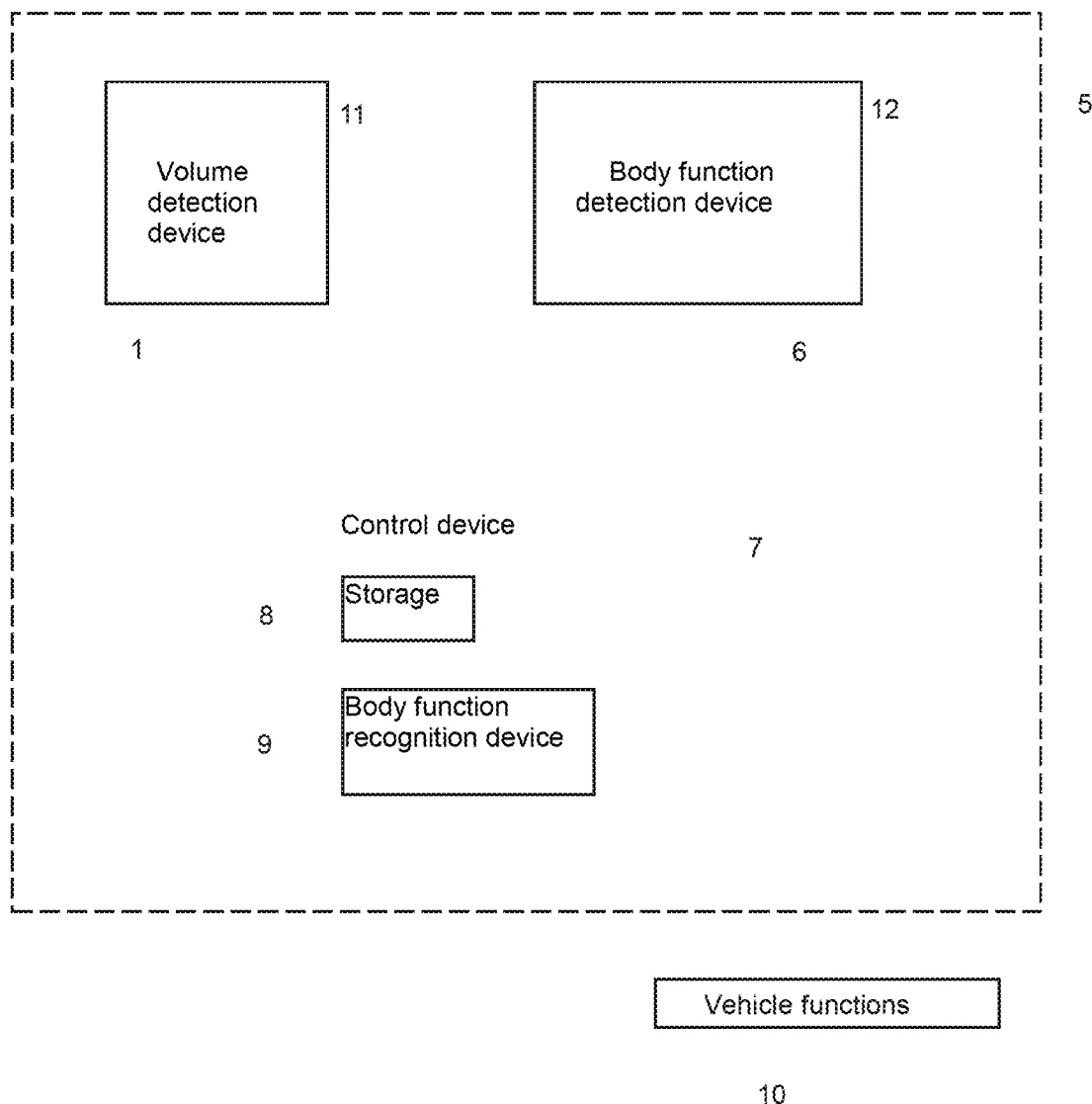
Figure 4:
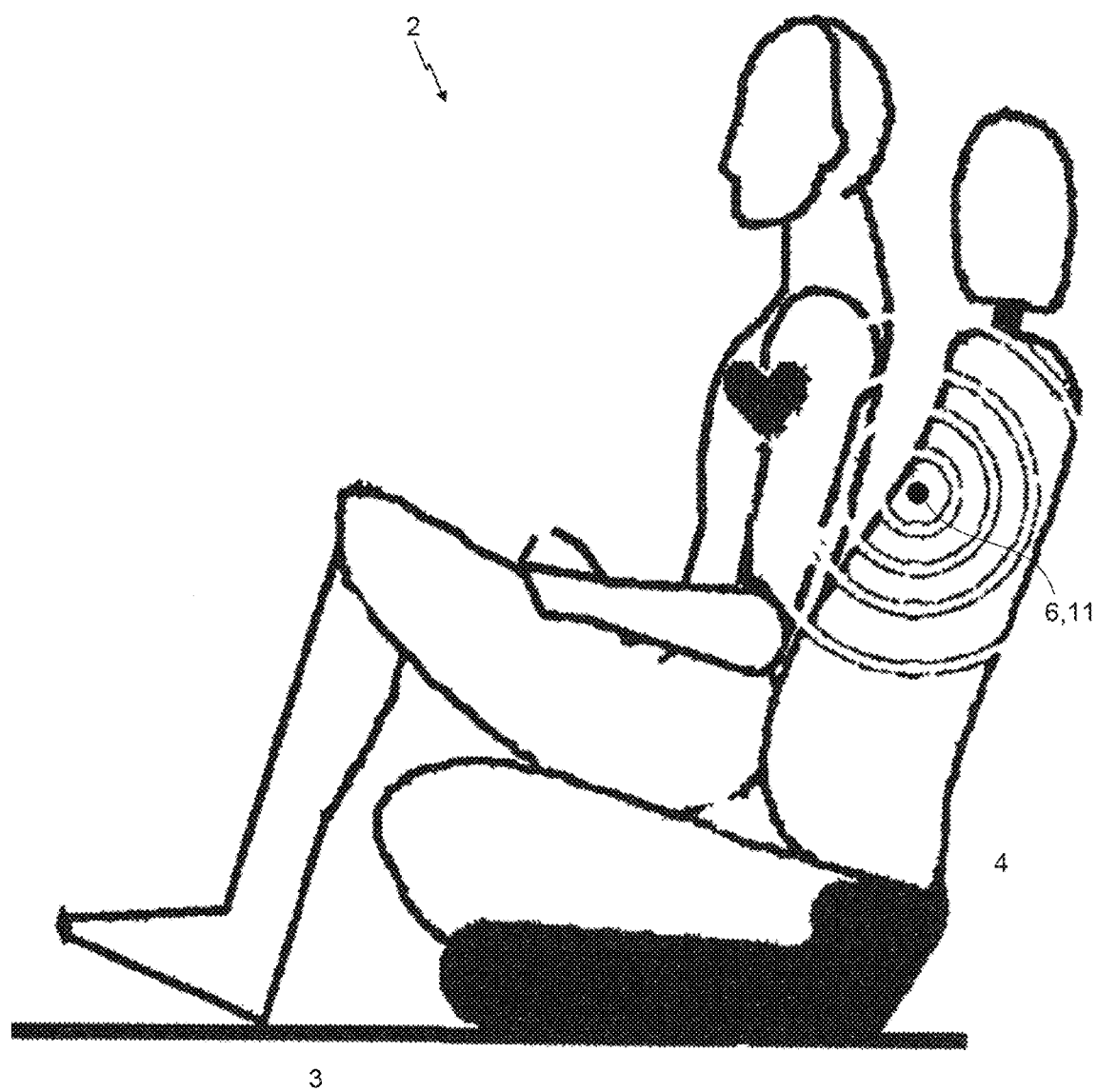
Figure 5A:
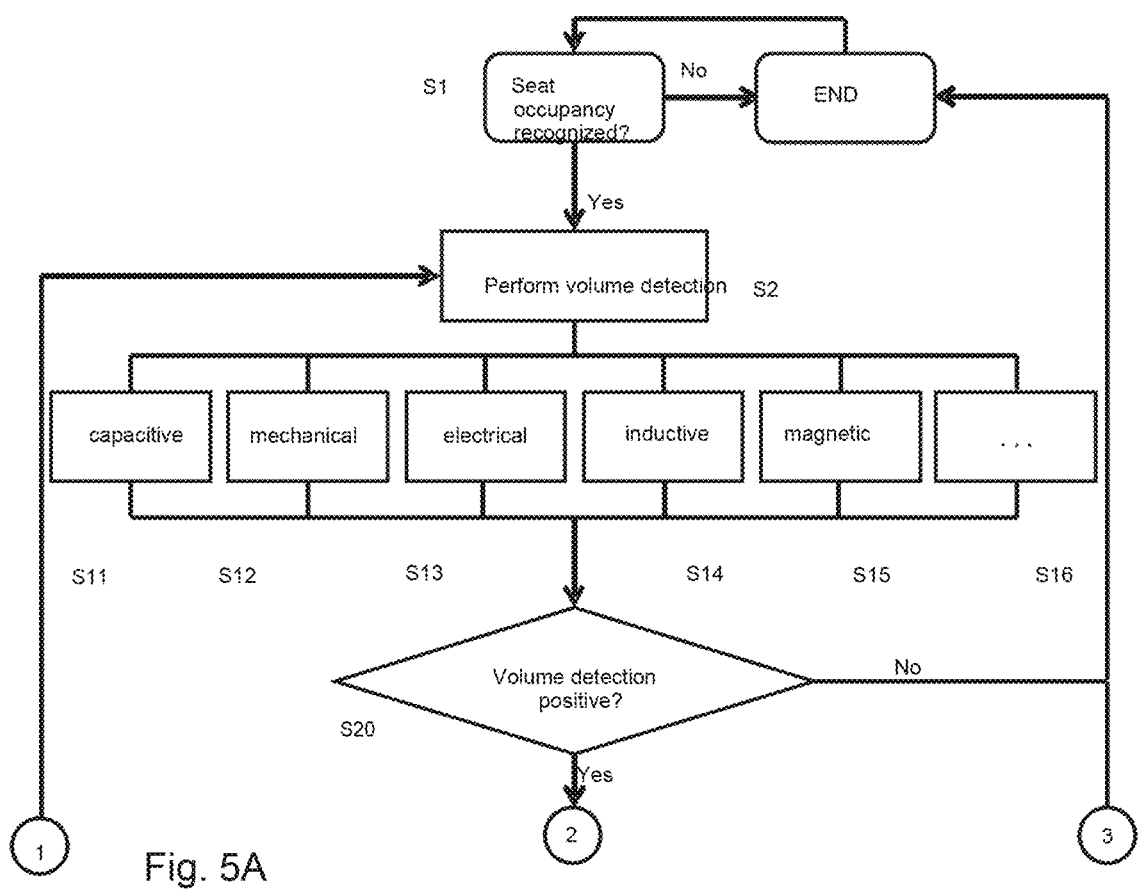
Figure 5B:
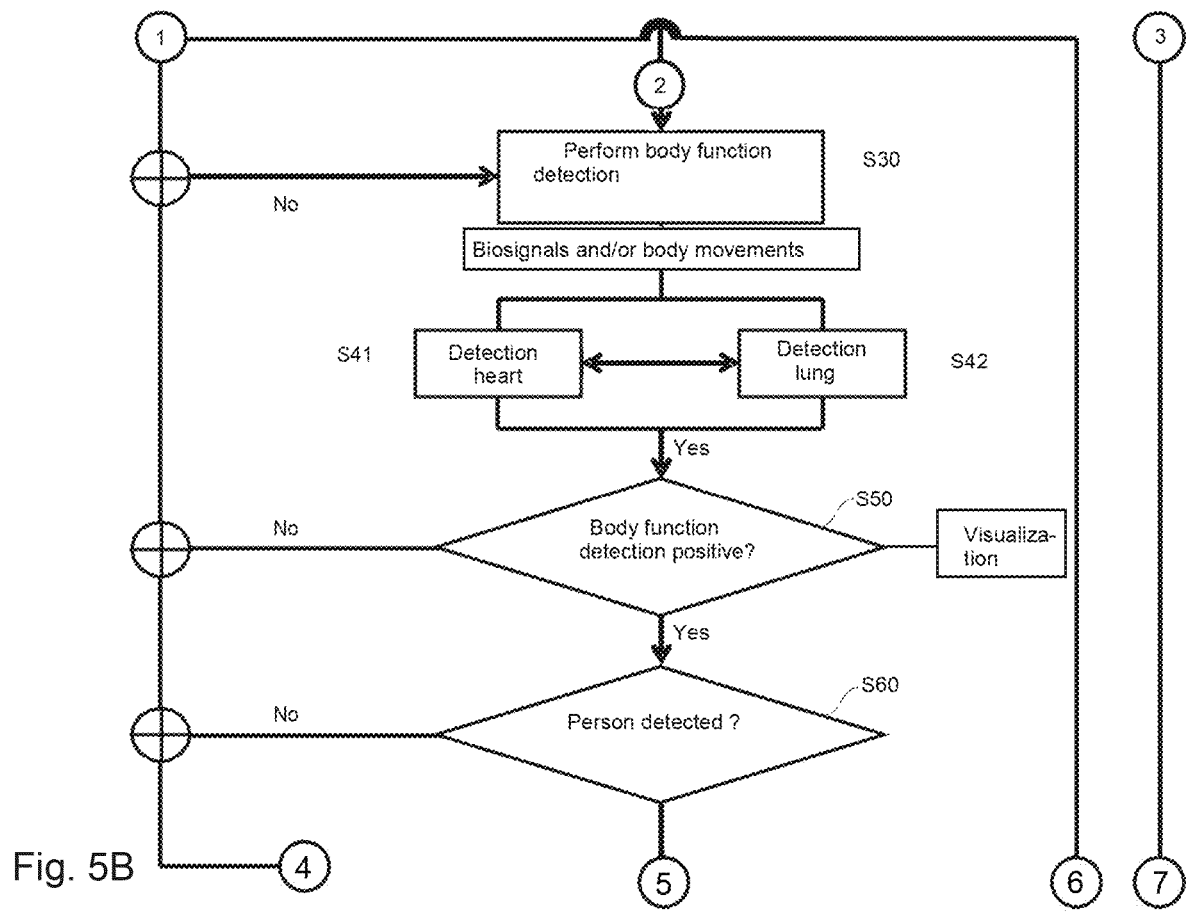
Figure 5C:
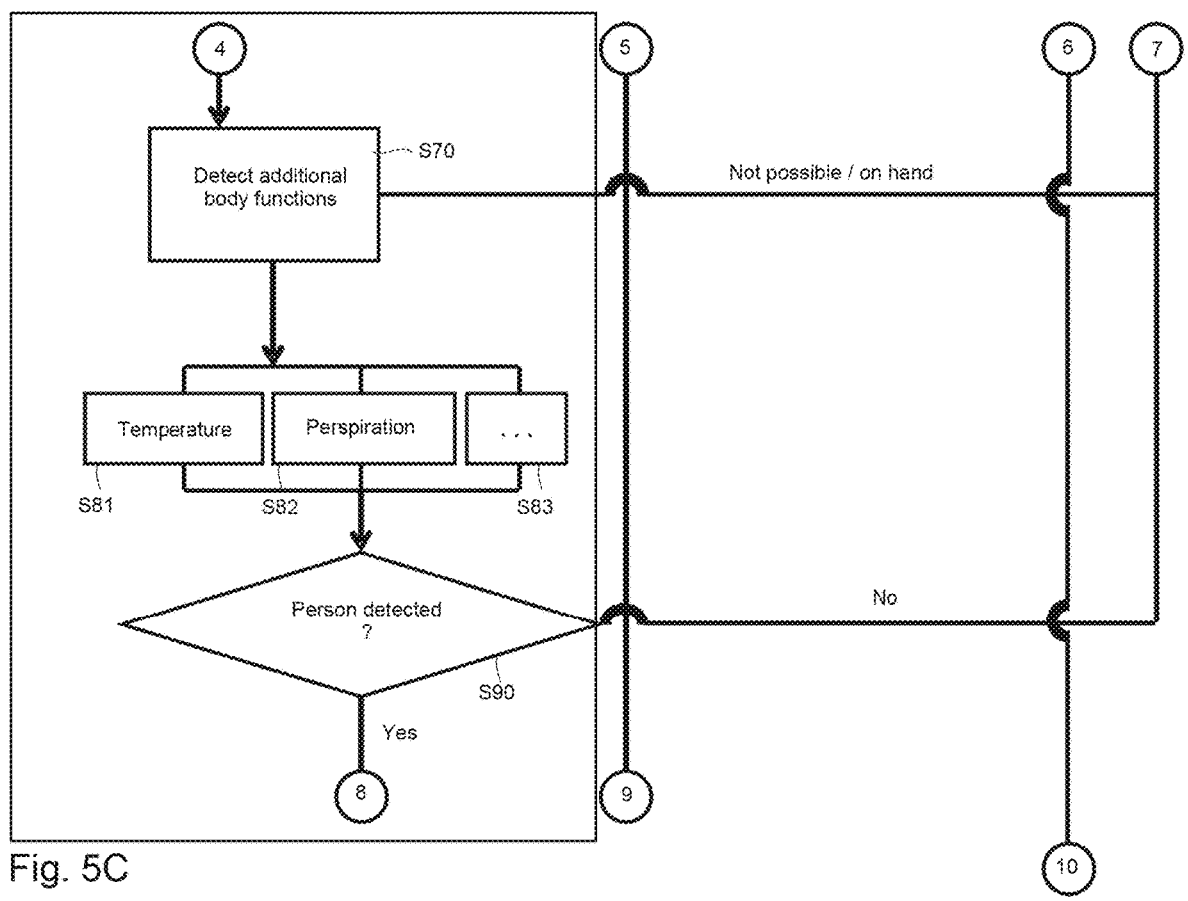

Additional objectives, advantages and expediences of the present invention are found in the following description in conjunction with the drawing. Depicted are:

FIG. 1A a vehicle seat with a possible detectable volume;
FIG. 1B the vehicle seat according to FIG. 1A in a top view;
FIG. 1C the vehicle seat according to FIG. 1A in a front view;
FIG. 1D the vehicle seat according to FIG. 1A in a side view;
FIG. 2 a vehicle seat with a possible detectable volume and a volume to be detected;
FIG. 3 a seat occupancy recognition device according to a particularly preferred embodiment;
FIG. 4 contact-free measurement of a body function;
FIG. 5A-5D a method according to a particularly preferred embodiment.

FIG. 1A depicts a vehicle seat 2 and a possible detectable volume V in a perspective view, in which by means of a volume detection device 1 (not depicted here), one can detect a volume V' located within volume V. Volume V is located on vehicle seat 2 as shown and is approximately enclosed by a seat part 3 and a backrest part 4. Naturally, other volumes are also conceivable, wherein such a volume V is sensible since it is highly probable that vehicle drivers are located within this volume V if they wish to operate a vehicle. A volume, which includes a person or an object and is located in the detectable volume V can therefore be detected.

In this case, one cannot see any seat occupancy recognition device 5 in FIGS. 1A to 1D since these are preferably integrated in the vehicle seat 2 so as not to influence or impair the vehicle driver while driving or more generally when sitting.

FIG. 1B depicts the vehicle seat according to FIG. 1A in a top view, FIG. 1C in a front view, and FIG. 1D in a side view.

Naturally, other volume regions V are also conceivable, since a person also has or can have volume elements V' outside of volume V shown in FIGS. 1A-1D.

FIG. 2 hereby depicts once again possible volume V, wherein volume V', depicted by a cross-hatched surface/cross-hatched volume, can be detected for a person sitting on the vehicle seat 2.

FIG. 3 depicts a possible design here of the seat occupancy recognition device 5, comprising a volume detection device 1 having a first sensor 11, a body function detection device 6 having a second sensor 12, wherein volume detection device 1 and body function detection device 6 are each connected at least in a signal-related manner to a control device 7. Control device 7 comprises in this case a storage unit 8 and a recognition device 9 or a body function recognition device 9.

Furthermore, seat occupancy recognition device 5, particularly control device 7, is advantageously connected at least in a signal-related manner to the respective vehicle functions 10 to release or block respective vehicle functions 10, depending on whether seat occupancy recognition has been positive or negative.

It is also conceivable that storage unit 8 and recognition device 9 are not integrated in control device 7, but are independent devices, which are connected at least in a signal-related manner to control device 7.

Advantageously, both volume detection device 1 as well as body function detection device 6 are designed in such a manner that they can detect the corresponding values in a contact-free manner. In particular, the corresponding first sensor 11 is designed to perform contact-free detection.

FIG. 4 schematically shows such a contact-free measurement of a body function, in this case 3o detecting a cardiac function, particularly a heart rate. As one can see, body function detection device 6, particularly second sensor 12, is integrated in backrest 4, whereas in an alternative or cumulative manner, an arrangement can be integrated in seat part 3 or any other element of vehicle seat 2 or also the vehicle itself.

Various options for contact-free detection or measurement of a volume or a body function respectively are known from prior art. These may be designed in an electric, electronic, capacitive, ultrasound-based, mechanical, magnetic, electromagnetic, acoustic, optical, thermal manner and the like. Preferably, capacitive methods are preferred since these have a very simple structure and are very precise.

Preferably, cardiac and/or pulmonary activity of the person on vehicle seat 2 is/are detected by the second sensor 12. Furthermore, it is conceivable to also measure the temperature and/or perspiration of the person, for example by an additional second sensor 12.

A possible process sequence for seat occupancy recognition is shown and described in FIGS. 5A-5D.

First, it is determined in a step S1, preferably by seat occupancy recognition device 5, whether seat occupancy recognition is necessary or not. If it is not necessary, the sequence is discontinued and restarted if applicable. A need may hereby exist if the vehicle is to be activated, controlled or the like. In these cases, it is particularly important that a vehicle driver is on vehicle seat 2 for these activities in order to perform the corresponding movements. This can be recognized by corresponding sensors and/or a control unit that a vehicle driver is operating or wishes to operate vehicle functions.

If it is detected that seat occupancy recognition must be performed, one continues with step S2, wherein step S2 corresponds to volume detection. It can be carried out in various ways, for example capacitively S11, mechanically S12, electrically S13, inductively S14, magnetically S15 or in another way S16, wherein capacitive volume detection is preferred. Detection by means of soundwaves or optical recognition is also conceivable.

If volume detection S2 was performed using one way or a combination of ways of S11 to S16, seat occupancy recognition device 5 decides in a subsequent step S20, whether a volume was detected or not. If the decision is negative, the sequence is discontinued here and restarted if applicable. A decision is based on the measurement values of the first sensor.

However, if volume detection S20 is positive, in other words if there is a volume V' in detection range V, then a body function detection is initiated in a step S30 by means of the seat occupancy recognition device 5. Body function detection can hereby be performed by detecting biosignals and/or movements, particularly of the cardiac functions/a pulse S41 and/or detecting the pulmonary functions S42. Naturally, it is also conceivable to utilize other body functions, instead of the cardiac or pulmonary functions, wherein the cardiac and pulmonary functions are preferably measured. It is hereby also conceivable to recognize biosignals, such as cardiac or pulmonary functions on the one hand, and/or detect body movements on the other.

After performing a detection for cardiac function S41 and/or detection for pulmonary function S42, the result is subsequently evaluated and verified in a step S50. If the body function detection is negative, depending on the programming, either detecting the body functions S30 is carried out again or the sequence is continued again by carrying out a volume detection S2. If the body function detection was positive, the recorded data of the body function detection can be visualized correspondingly, for example by means of a display or the like. In addition, the data can be documented, in other words stored, to be later evaluated or utilized in the event of an accident.

However, if measuring the body functions is positive, in other words if the corresponding body functions were detected, it must be decided and recognized in a step S60, whether it is a person or another animate being, such as an animal, that is sitting on the vehicle seat.

For example, if it was recognized in step S60 that a person is not involved, various further handling options can be utilized.

Thus, it is conceivable for example to restart and run through body function detection S30 once again to exclude possible errors. Alternatively, it is conceivable to do a restart already in step S2 of volume detection and to run through the entire seat occupancy recognition process again.

However, it is also conceivable to measure additional body functions in a step S70, for example a temperature in a step S81, perspiration in a step S82, wherein other body functions S83 are also conceivable.

If it is not possible to measure additional body functions in a step S70, the sequence is ended and restarted. This also applies when no person is detected in a step S90.

However, if in a step S90 it is recognized that a person is involved, then seat occupancy recognition is positive S100. If a positive seat occupancy S100 was recognized, seat occupancy recognition is restarted directly afterward, preferably with volume detection step S2, wherein naturally other start positions are also conceivable, such as whether seat occupancy was recognized S1 or body function detection S30 was performed. By means of positive seat occupancy recognition, it is now also possible for the driver to activate or deactivate corresponding vehicle functions. This includes for example starting the vehicle and operating the seat heater, ventilation, the air-conditioning system, and so on.

Furthermore, after seat occupancy recognition was positive, the corresponding recorded sensor data is stored in a step S101, preferably in storage device 8. This storing enables one to retrieve the sensor data at later points in time and to use it for other functions and purposes.

In an additional step S102, additional sensor data is continually tapped or recorded, and naturally also stored. As a result, it is possible to depict a trend of body functions and to compare it against currently recorded sensor data.

By this comparison, one can recognize for example a health status or driving ability status that deviates from the norm. For example, if the driver is under stress, generally the heart rate and breathing rate increase. An increase of these rates can be recognized in a particularly simple manner by a comparison against previously recorded sensor data. Likewise, one can recognize for example that the heart and breathing rate are decreasing, which then points to the fact that the person on the vehicle seat is becoming tired. If such a health status or driving ability status is not recognized, then sensor data will continue to be recorded and a detection of the health status or driving ability status will continue to be performed.

By detecting a health status or driving ability status, one can make inferences about the vehicle driver's driving ability. If the health status deviates drastically compared to a normal status, the driving ability of the vehicle driver can be revoked and the vehicle functions can 3o be deactivated by the seat occupancy recognition, i.e., the vehicle driver can no longer activate any of the vehicle functions.

A health status or a driving ability status can be determined in particular by comparing current data against previously recorded data. In particular, by comparing current data against previously recorded data, one can also determine a trend, for example whether the driver is becoming tired or the like. Advantageously, a comparison is performed with a recorded or a previously stored starting value; a trend or a comparison using the health status of the driver is therefore determined at the start of the activity.

Advantageously, after recognizing the deviating health status or driving ability, a suggestion regarding rectification can be conveyed by seat occupancy recognition device 5, which is communicated to the person visually and/or acoustically, for example shown on a display or indicated by means of a spoken warning. For example, if a person perspires profusely, seat occupancy recognition device 5 can suggest to the person to activate the air-conditioning system. It is thereby particularly advantageous that seat occupancy recognition device 5 does not automatically activate the air-conditioning system, but first only communicates the suggestion to the person. The person must then either reject or accept the suggestion. If the person rejects the suggestion, the suggestion is not executed; if the suggestion is accepted on the other hand, the suggestion is executed, in other words the air-conditioning system is activated for example. Such a decision is carried out in a step S105. However, it is also conceivable that an automatic activation or deactivation of vehicle functions is undertaken by seat occupancy recognition device 5 and the vehicle driver receives a visual or acoustic notification about it, for example a sign via a display or a signal tone.

Alternatively, it is also conceivable that both volume detection as well as the body function detection are performed simultaneously and not sequentially as described above. Four different combinations then result from this: positive volume detection and body function detection, negative volume detection and body function detection, negative volume detection and positive body function detection, and positive volume detection and negative body function detection.

If volume detection and body function detection are positive, it shall be inferred that an animate being is on the vehicle seat. Preferably, one can also recognize by means of detection device 9, whether the animate being is a person or not.

If volume detection and the body function detection are negative, it shall be concluded that the vehicle seat is not occupied.

If volume detection is negative and the body function detection is positive, it shall be concluded that a person is in the vicinity of the body function detection device 6, but is not sitting on vehicle seat 2 itself. For example, the person could be behind vehicle seat 2.

If volume detection is positive and the body function detection is negative, it is to be assumed that an inanimate object is on the vehicle seat.

Positive seat occupancy recognition hereby also occurs when the volume detection and the body function detection were positive.

Alternatively, it is also conceivable to first perform a body function detection and to perform volume detection after the body function detection.

Positive seat occupancy recognition hereby also occurs only when the volume detection and the body function detection were positive.

All features disclosed in the application documents are claimed as essential to the invention, to the extent they are novel individually or in combination in relation to prior art.

LIST OF REFERENCE SIGNS

1 Volume detection device
2 Vehicle seat
3 Seat part
4 Backrest part
5 Seat occupancy recognition device
6 Body function detection device
7 Control device
8 Storage device
9 Body function detection device
10 Vehicle function
11 First sensor
12 Second sensor
13 Display
V, V' Volume

What is claimed is:

1. A method for recognizing the seat occupancy of a seat, comprising:
   a. Performing a volume detection process for detecting a volume on a vehicle seat by a volume detection device, wherein the seat comprises the volume detection device,
   b. Performing a body function detection process by a body function detection device only after positive volume detection, wherein the seat comprises the body function detection device,
   c. Performing a body function recognition process by a body function recognition device only after positive body function detection, wherein the body function recognition process comprises at least one process of detecting a cardiac function and detecting a pulmonary function, wherein the seat comprises the body function recognition device,
   wherein after a negative body function recognition, either:
      (i) the body function detection process is performed again,
      (ii) one continues with method step a., or
      (iii) at least one additional body function is detected by the body function detection device.

2. The method according to claim 1,
further comprising:
the at least one additional body function is selected from a group which comprises detecting a temperature, perspiration, gastric acoustics, body odor and brain waves and/or a combination of these.

3. The method according to claim 1,
wherein
data that is recorded by the body function detection device is shown by a display.

4. The method according to claim 1,
wherein
a health status is detected by the body function recognition device after positive body function recognition.

5. A vehicle seat comprising:
a seat occupancy recognition device for recognizing seat occupancy of a seat,
having:
at least one volume detection device having a first sensor, which is provided and designed for detecting a volume on the vehicle seat, and at least one body function detection device having a second sensor, which is provided and designed for detecting body functions, and at least one body function recognition device for recognizing the detected body functions, the volume detection device and the body function detection device being connected to a control device, the control device operating the body function detection device only in response to receiving signal from the volume detection device indicating that volume on the vehicle seat has been detected.

6. The vehicle seat according to claim 5,
wherein
by the first sensor of the volume detection device, at least one process of contour detection and mass detection can be performed.

7. The vehicle seat according to claim 5,
wherein
by the second sensor of the body function detection device, at least one of the functions of the cardiac function and pulmonary function can be detected.

8. The vehicle seat according to claim 5,
wherein
the seat occupancy recognition device has a storage device by which the sensor data, which can be recorded by the body function detection device, can be stored.

9. The vehicle seat according to claim 5,
wherein
the second sensor is designed and provided to record sensor data and transmit these to the body function recognition device, wherein a comparison of the sensor data against previously recorded sensor data can be performed by the body function recognition device to determine a health status.

10. The vehicle seat according to claim 5,
wherein
the first sensor and the second sensor are each selected from a group that comprises an optical, electrical, magnetic, electromagnetic, thermal, capacitive, acoustic or mechanical sensor.

11. The method according to claim 1, further comprising:
providing a storage device by which the sensor data, which can be recorded by the body function detection device, can be stored, and wherein a notice of vehicle functions and/or vehicle seat functions is provided in response to the stored sensor data.

12. The method according to claim 1, wherein the seat occupancy recognition is performed in response to an activated vehicle function.

13. The vehicle seat according to claim 5, wherein the seat occupancy recognition device is integrated in a vehicle seat.

14. The vehicle seat according to claim 5, wherein the at least one body function recognition device is connected to the control device, the control device operating the at least one body function recognition device only in response to receiving a signal from the body function detection device indicating a positive body function detection,
wherein after a negative body function recognition, either:
(i) the body function detection device detects a body function again,
(ii) the volume detection device detects the volume on the vehicle seat again, or
(iii) at least one additional body function is detected by the body function detection device.

* * * * *